(12) United States Patent
Alleyne

(10) Patent No.: US 9,232,937 B2
(45) Date of Patent: Jan. 12, 2016

(54) REARCHITECTING THE SPINE

(75) Inventor: Neville Alleyne, Oceanside, CA (US)

(73) Assignee: Elite I.P., Inc., Carlsbad, CA (US)

( * ) Notice: Subject to any disclaimer, the term of this patent is extended or adjusted under 35 U.S.C. 154(b) by 1280 days.

(21) Appl. No.: 12/579,304

(22) Filed: Oct. 14, 2009

(65) Prior Publication Data

US 2010/0094298 A1    Apr. 15, 2010

Related U.S. Application Data

(60) Provisional application No. 61/105,359, filed on Oct. 14, 2008.

(51) Int. Cl.
*A61B 17/02* (2006.01)
*A61B 17/16* (2006.01)
*A61B 17/00* (2006.01)

(52) U.S. Cl.
CPC .......... *A61B 17/025* (2013.01); *A61B 17/1671* (2013.01); *A61B 2017/00557* (2013.01); *A61B 2017/0256* (2013.01); *A61B 2017/0262* (2013.01)

(58) Field of Classification Search
CPC ..................... A61F 9/00763; A61B 17/32002; A61B 17/1671
USPC ....... 606/79, 80, 86 R, 85, 171, 180; 600/207
See application file for complete search history.

(56) References Cited

U.S. PATENT DOCUMENTS

| 3,937,222 A * | 2/1976 | Banko ............................ 606/170 |
| 5,667,509 A | 9/1997 | Westin |
| 5,769,865 A | 6/1998 | Kermode et al. |
| 5,904,681 A * | 5/1999 | West, Jr. .......................... 606/41 |
| 6,626,905 B1 | 9/2003 | Schmiel et al. |
| 6,684,886 B1 | 2/2004 | Alleyne |
| 7,033,392 B2 | 4/2006 | Schmiel et al. |
| 7,070,596 B1 * | 7/2006 | Woloszko et al. .............. 606/41 |
| 7,189,240 B1 | 3/2007 | Dekel |
| 7,204,851 B2 | 4/2007 | Trieu et al. |
| 8,328,810 B2 * | 12/2012 | Patel et al. ...................... 606/79 |
| 2002/0107521 A1 | 8/2002 | Petersen et al. |
| 2002/0151894 A1 | 10/2002 | Melkent et al. |
| 2002/0173795 A1 * | 11/2002 | Sklar ............................... 606/80 |

(Continued)

FOREIGN PATENT DOCUMENTS

| WO | WO 99/29253 | 6/1999 |
| WO | WO 03/092507 A2 | 11/2003 |

(Continued)

OTHER PUBLICATIONS

Extended European Search Report in Application No. 09821215.2, dated Jun. 28, 2013.

(Continued)

*Primary Examiner* — Andrew Yang
(74) *Attorney, Agent, or Firm* — Knobbe Martens Olson & Bear LLP

(57) ABSTRACT

A surgical tool well suited for less invasive surgery. Uses include spinal surgery and microdecompressive techniques. The method and device are useful for rearchitecting the spine. A cutting tip or head on a shaft is shielded during non-use to protect tissue and neural elements. To further protect neural elements and tissue, an inflatable retractor is introduced into the body with the surgical tool.

13 Claims, 8 Drawing Sheets

(56) References Cited

U.S. PATENT DOCUMENTS

| | | |
|---|---|---|
| 2003/0073998 A1 | 4/2003 | Pagliuca et al. |
| 2004/0030222 A1 | 2/2004 | Suddaby |
| 2004/0181251 A1* | 9/2004 | Hacker et al. .............. 606/170 |
| 2005/0165420 A1 | 7/2005 | Cha |
| 2005/0197661 A1 | 9/2005 | Carrison et al. |
| 2005/0209622 A1 | 9/2005 | Carrison |
| 2005/0216085 A1 | 9/2005 | Michelson |
| 2005/0277968 A1 | 12/2005 | Lee |
| 2006/0004369 A1 | 1/2006 | Patel et al. |
| 2006/0089609 A1* | 4/2006 | Bleich et al. .............. 604/272 |
| 2006/0142775 A1* | 6/2006 | Heneberry et al. ........... 606/80 |
| 2006/0200155 A1* | 9/2006 | Harp .......................... 606/85 |
| 2006/0200238 A1 | 9/2006 | Schmiel et al. |
| 2006/0264957 A1* | 11/2006 | Cragg et al. ................ 606/80 |
| 2006/0264994 A1 | 11/2006 | Schomer et al. |
| 2008/0065125 A1* | 3/2008 | Olson ....................... 606/159 |
| 2008/0243125 A1 | 10/2008 | Guzman et al. |
| 2009/0204119 A1 | 8/2009 | Bleich et al. |

FOREIGN PATENT DOCUMENTS

| | | |
|---|---|---|
| WO | WO 03/092507 A3 | 11/2003 |
| WO | WO 2004/008976 | 1/2004 |
| WO | WO 2004/019785 | 3/2004 |
| WO | WO 2004/080316 | 9/2004 |
| WO | WO 2005/051246 A2 | 6/2005 |
| WO | WO 2005/051246 A3 | 6/2005 |
| WO | WO 2005/062827 | 7/2005 |
| WO | WO 2006/047598 | 5/2006 |
| WO | WO 2007/075152 | 7/2007 |

OTHER PUBLICATIONS

Translated Office Action in Chinese Application No. 200980148340.6, dated Nov. 6, 2013.

Search Report in Chinese Application No. 200980148340.6, dated Nov. 6, 2013.

Office Action issued Jul. 10, 2014 in Chinese Application No. 200980148340.6.

* cited by examiner

REARCHITECTING THE SPINE

RELATED APPLICATIONS

This application claims priority to U.S. provisional patent application No. 61/105,359 entitled "DEVICE AND METHOD FOR OSTEOLIGAMENTOUS RESECTION" filed Oct. 14, 2008 the contents of which are hereby incorporated by this reference.

FIELD OF THE DISCLOSURE

This disclosure relates generally to minimally invasive orthopedic or neurosurgical devices and procedures to reconfigure portions of the spinal canal

BACKGROUND

Not uncommon with at least the aging population and many others are medical and physiological conditions such as acquired central and neural foraminal stenosis. It has been estimated by some that by the year 2030, approximately 45% to 50% of the population will be 65 or greater and with increased population age the condition of spinal stenosis and its clinical presentation of neurogenic claudication may continue to grow. Traditional treatment options include performing decompressive laminectomies, partial medial facetectomies, and/or partial foraminotomies in order to gain adequate decompression. Such procedures tend to result in some level of iatrogenic instability into the motion segments involved.

Other traditional treatment options may include fusion technology such as pedicle screw or segmental instrumentation posteriorly and/or interbody techniques such as posterior lumbar interbody fusion, lateral interbody fusion technology, TLIF (transforaminal interbody fusion), XLIF (extreme lateral interbody fusion), ALIF (anterior lumbar interbody fusion), DLIF (direct lateral interbody fusion), or GLIF, a perilinear approach to the anterolateral interbody region exists. These technologies, coupled with bone graft materials for fusion including, but not limited to, autologous bone, allograft bone, demineralized bone, bone morphogenetic proteins, growth factors, cement, gene therapy, and/or mesenchymal stem cells, have become more and more prevalent. Limited interbody fusion techniques such as interbody spacers that are capable of fusing one spinous process to the other, facet screws, facet bolts, or stand-alone cages may be used with a certain degree of bone graft material to allow the motion segment to be fused. Multilevel decompressions and fusions also are known to carry with them a greater risk for nonunion or pseudoarthrosis because of the number of motion segments attempting to be fused.

In the case of spinal stenosis pressure (compression) on the nerve, dura or thecal sac can lead to pain and discomfort which may limit walking, bending and deteriorate the quality of life. Pain and discomfort may also lead to the use of and narcotics, anti-inflammatory medications, muscle relaxers, epidural steroid injections, and physical therapy.

FIG. 1 illustrates a traditional surgical drill which may be used to treat the spinal canal. One commercially available example of such a device is the Ultrapower™ Surgical Drill System from Hall Surgical. The drill consists of a handpiece 10 connected at its proximal end to a power source, which may, for example, comprise compressed air (not shown). The hand piece 10 has a spindle 12 that rotates in response to actuation of the handpiece motor (not shown), which is driven by the power source. Attached to the front end of the handpiece 10 is a coupling assembly 14. The coupling assembly 14 releasable holds an accessory 16 to the spindle 12 so the accessory 16 rotates in unison with the spindle 12. The accessory 16, having a file, rasp or burr 18 at its distal end, is releasably coupled to a handpiece spindle 12. The cutting accessory 16 has a shaft 20, the proximal or rear end of which is releasably held to the spindle 12 by the coupling assembly 14.

The cutting accessory 16 typically stands past the distal tip of the surgical device 22. In this position, it is possible that the file, burr or rasp 18 could cause unintended injury. For example, because of the power of the tool, it is possible that the dura could be pulled into the working channel of the file, burr or rasp or other resecting instrument. If the neural tissue were pulled into the surgical drill, a neurologic catastrophe could result.

SUMMARY

In some exemplary implementations there is a surgical tool, system and method of use whereby a hand held tool in combination having a handle, a cutting means with a cutting tip and, an inflatable retractor which is situated on one side of the cutting means. The inflatable retractor has a top surface, bottom surface, outer surface and interior.

In some exemplary implementations dependant on many variables including the intended use, desired result, or area target region, the cutting tool may be a shaft driven burr, file, rasp, or other cutting tool. The shaft may impart to the cutting tool, at least one of reciprocating movement, rotational movement, vibrational movement or sway movement and side to side movement.

In some exemplary implementations there is a surgical tool, system and method of use whereby a hand held tool in combination having a handle, a cutting means with a cutting tip a resector shield which at least partially surround the cutting tool, and, an inflatable retractor which is situated on one side of the cutting means. In some circumstances the shield is movable relative to the cutting tool. The movability of the resector shield is used to at least one of dissect tissue, retract tissue and expose the target area to the cutting tool for resection. When unexposed or shielded the tissue and neural elements are protected from the cutting tool.

In some aspects the inflatable retractor means is a single chamber or bladder. The inflatable retractor means has an inner surface and outer surface and the outer surface has portions facing the resector and portions facing away from the resector. The outer surface of the inflatable retractor means may be textured or shaped. Portions of the inflatable retractor means may be of non-homogeneous materials which have properties that are diverse. Diverse properties may include stiffness, resistance to cuts or tears, hardness, coefficient of friction, softness, slickness, lubricity. Inflated properties are variable and can control stiffness, softness, bendability and size of the inflatable retractor means.

In some aspects the inflatable retractor means is two or more chambers or bladders. The inflatable retractor means may share an internal wall forming the chambers or the chambers may be separated and have no coextensive wall. The multi-chambered inflatable retractor means has an inner surfaces in the chambers or bladders and one or more outer surfaces and the outer surface(s) generally have portions facing the resector and portions facing away from the resector. The outer surface of the entire inflatable retractor means may be textured or shaped. The outer surface of the chambers of the inflatable retractor means may each be textured or shaped. Portions of the multi-chambered inflatable retractor means may be of non-homogeneous materials which have properties that are diverse. Diverse properties may include stiffness, resistance to cuts or tears, hardness, coefficient of friction, softness, slickness, lubricity. Inflated properties are variable and can control stiffness, softness, bendability and size of the inflatable retractor means. In some instances the chambers are in fluid communication. In other instances the chambers are not in fluid communication.

Devices and methods disclosed herein include, but are not limited to, a system or tool for performing resection of a portion of the spine, by introducing a surgical tool that in combination has at least a body or handle / hand piece on which is supported or affixed a shaft mounted cutting tip for resection and a selectively inflatable retractor. During use the inflatable retractor is used to protect and/or retract at least one neural element. The resector is used to remove at least one of bone and ligament with the cutting tip.

Devices and methods disclosed herein include, but are not limited to, a system or tool for performing resection of a portion of the spine, by introducing a surgical tool that in combination has at least a body or handle/hand piece is supported or affixed a shaft mounted cutting tip for resection, a resector shield that movably exposes and unexposes the cutting tip and a selectively inflatable retractor. During use the inflatable retractor is used to protect and/or retract at least one neural element. The resector is used to remove at least one of bone and ligament with the cutting tip. One or more portions of the resector shield provide protection of tissue from cutting tip damage, can be sued to dissect and to retract.

BRIEF DESCRIPTIONS OF THE DRAWING

DETAILS OF THE DISCLOSURE

Definitions

Figure 1:
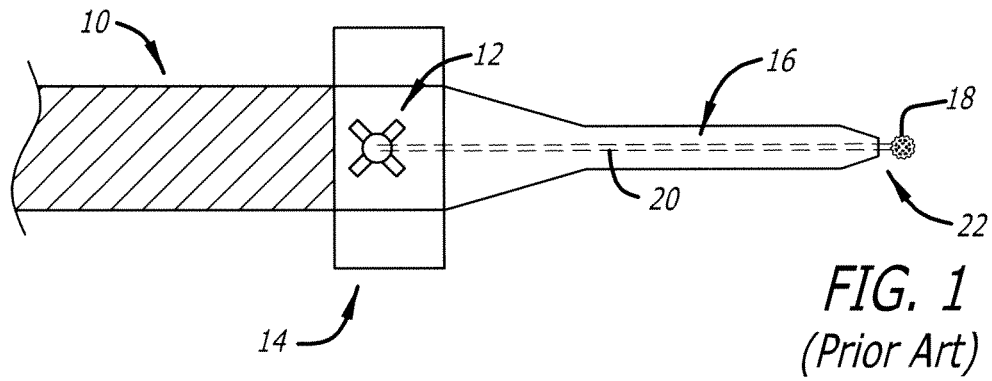
FIG. 1 is an illustration of an unprotected surgical drill.

1. Microdissection means a cut or stab incision which has the following characteristics the incision is generally less than 14 mm.

2. Re-engineering and/or rearchitecting the spine refers to modifying existing structural elements of the spine (without complete removal) to provide more space in which the nerves reside.

3. Neural elements means nerves, dura, thecal sac, and associated functional and structural elements.

4. Fluid Communication means a fluid such as air, gas, water or a mixture of same passing between chambers or bladders wherein changes in, the temperature, volume, flow rate or pressure of the fluid in one bladder or chamber is also occurs in chamber or bladder being which is connected thereto. Connected as used in this definition may be, but does not require, being directly adjacent or sharing a common wall.

In the following description, various exemplary implementations, aspects and characteristics are discussed as directed toward surgical instruments, tools, systems and methods more particularly applied to the spine. The focus on this application is not intended to be, nor should it act as, a limitation to the scope of this disclosure. The other features and advantages of the present disclosure will be set forth, in part, in the descriptions which follow and the accompanying drawings, wherein the implementations of the present disclosure are described and shown, and in part, will become apparent to those skilled in the art upon examination of the following description taken in conjunction with the accompanying drawings or may be learned by practice of the present disclosure.

Heading and Titles are not intended to be limitations and should be read in a general sense. Implementations may include several novel features, no single one of which is solely responsible for its desirable attributes or which is essential to practicing the disclosure described herein. The advantages of the present disclosure may be attained by means of the instrumentalities and combinations particularly pointed out in the disclosure and any appended claims.

Generally disclosed is a tool and device useful in treating living systems. The tool and device may be used within a system which in some instances is used to remove organic material within a subject's body. The removal of the organic material can be part of a method of treatment. The removal of organic material may be part of a re-engineering of a portion of a section of a subject's body.

A micro dissection in the context of the spinal canal is a procedure which reduces destabilizing the spine in comparison to traditional surgeries. In such a micro dissection within the spinal canal a midline incision to the spine is made. The incision provides access between the interspinous processes down through the interspinous ligament and through the area between the lamina. The access allow insertion of a surgical tool which maybe used to resect at least a portion of the ligamentum flavum, bone, ligament, synovial lining and tissue within the spinal canal and/or neural foramen. Such a resection can promote internal decompression of at least one of lamina and the spinal laminar junction by increasing at least a region of a cross-sectional area within the spinal canal. With removal of at least one of the ligamentum flavum, bone, ligament, synovial lining and tissue the cross-sectional diameter within the neural foramen or in the spinal canal can be enlarged without performing a formal laminectomy or laminotomies.

The resection enlarges, at least a portion of, the cross-sectional diameter within a spinal canal. In the case of spinal stenosis if a neural element is impacted by the stenosis enlarging the spinal canal may relieve symptoms.

The enlargement methodologies are applicable to any condition in which the removal of at least one of bone, ligament and tissue can relieve compression on a neural element.

In some instances increasing the spinal canal diameter may reduce symptoms of neurogenic claudication. In some instance increasing the spinal canal diameter to address moderate stenosis may bring the canal, at least in part, to a substantially and normal cross-sectional diameter.

Figure 2A:
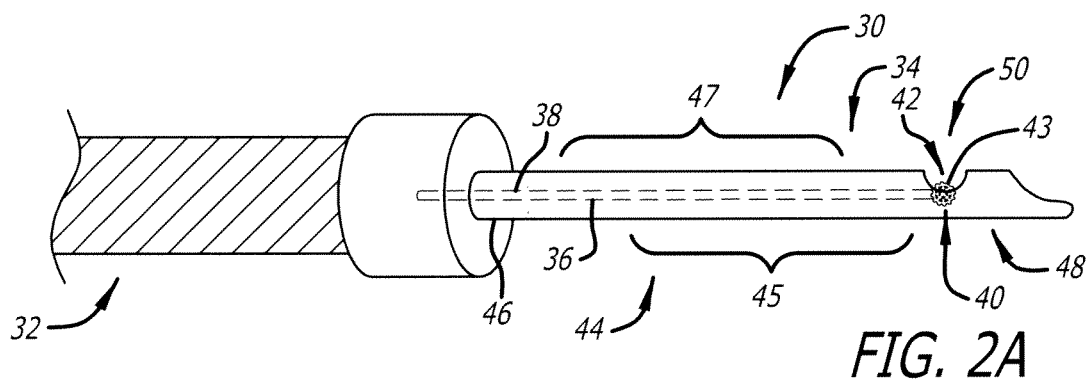
FIGS. 2A-2B are perspective views of some aspects of Applicants co-pending surgical tool and system disclosures in U.S. patent application Ser. No. 11/017,150.
Figure 2B:
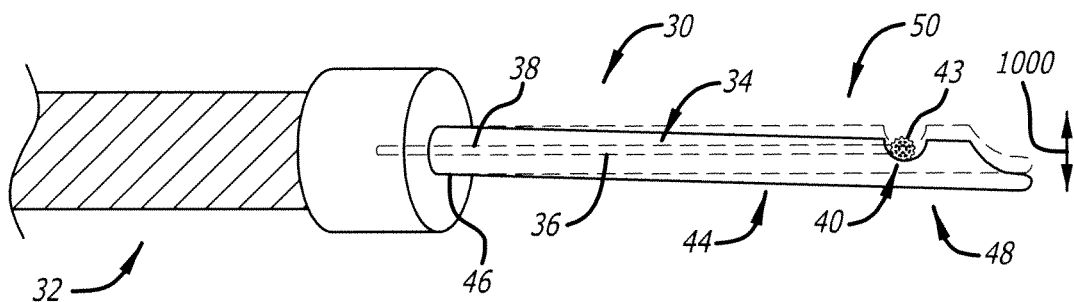

Turning now to FIGS. 2A and 2B, there is shown a resecting tool 30. The resecting tool provides a body such as a handpiece 32 and a resector 34 releasably coupled thereto. The resector 34 has a shaft 36 with a proximal end 38 and a distal (remote) end 40. At the distal (remote) end of the resector 40 is a resecting tip 42 generally referred to as a cutting tip.

In some exemplary implementations the resecting tool 30 includes a movable retractor 44 which also acts as a sheath. The movable retractor 44 has a top or ventral side 45 a proximal end 46, a bottom or dorsal side 47 and a distal (remote from the handpiece) end 48 and an inner and outer surface. The proximal end 46 of the retractor is movably fixed to the support such as the handpiece. The retractor 44 at least partially surrounds the resector 34, and at least part of the retractor 44 is moveable relative to the resector 34, at least along the line of arrow 1000. The burr 43 at the distal end of the resector 34 can be fully encased or partially encased at the distal end of the device by the retractor 44. The retractor 44 further comprises an opening 50 at its distal end 48 through which the resecting tip 42 will be exposed when the resector is moved downward relative to the resecting tip 42. In this implementation a burr 43 is movably mounted to the resecting tip 42, this will allow the burr 43 on the resecting tool 30 to remove bone, ligament, or other tissues while providing at least some protection for the surrounding neural elements on the ventral side 45 of the retractor 44. By keeping the dorsal side of the retractor 47 against the tissue needing to be resected and having the ventral side capable of retracting the surrounding tissue away from the site where resection is occurring, unattended tissue damage may be reduced.

During use, the process includes an actuator such as a foot pedal, button, or other device to start the burr in motion in response to compressed air pressure in the handpiece. Air pressure, gears, motors, levers, wheels, belts and the like may be used to rotate, tilt or deflect the retractor 44 to expose the burr tip 43. In this implementation, a switch, such as a trigger may be dual function to both start the resection and move the retractor. Alternatively, those of ordinary skill in the art will recognize that different triggers may separately operate the systems and part.

The resector itself 34 may include disposable/replaceable burrs 43 or other cutting (shaping) resecting tips 42. A non-exclusive list of such cutting devices includes high-speed burrs, files, blades, rasps, and reamers. Some cutting devices may undergo a rotational movement, some vibrate, some slide, while others may undergo a reciprocating movement, yet others may combine movement both rotationally and reciprocating. Cutting instruments may be powered with air pressure, via electric motors, belts, cables and the like.

In some exemplary implementations the cutting (shaping) resecting tips 42 are at least partially encased by the retractor 44. By at least one of moving the resecting tip into a position within the retractor 44 and moving the retractor upward to shield at least a portion of the resector tip, the cutting surface of the resector tip is less likely to engage vital structures such as neural elements and blood vessels (epidural veins). The retractor 44 not only is available to apply pressure to retract but also shields the resector. Thusly, the distal (remote) end 48 of the retractor preferably extends beyond the distal end 42 of the resector.

Figure 3:
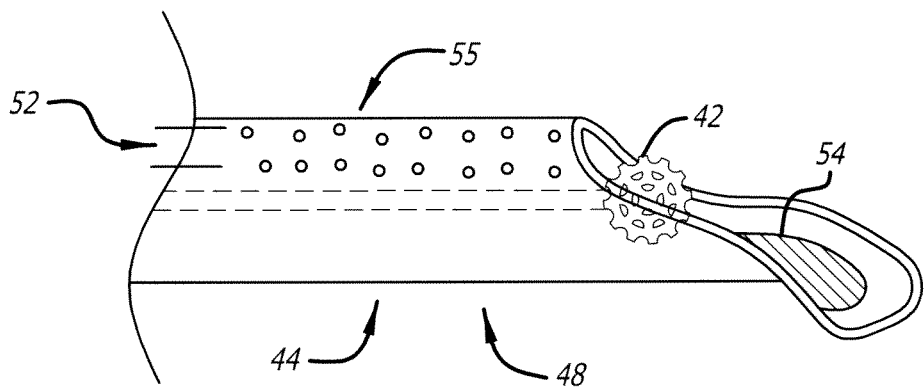
FIG. 3 illustrates an exemplary implementation of an end of a surgical tool.
Figure 4A:
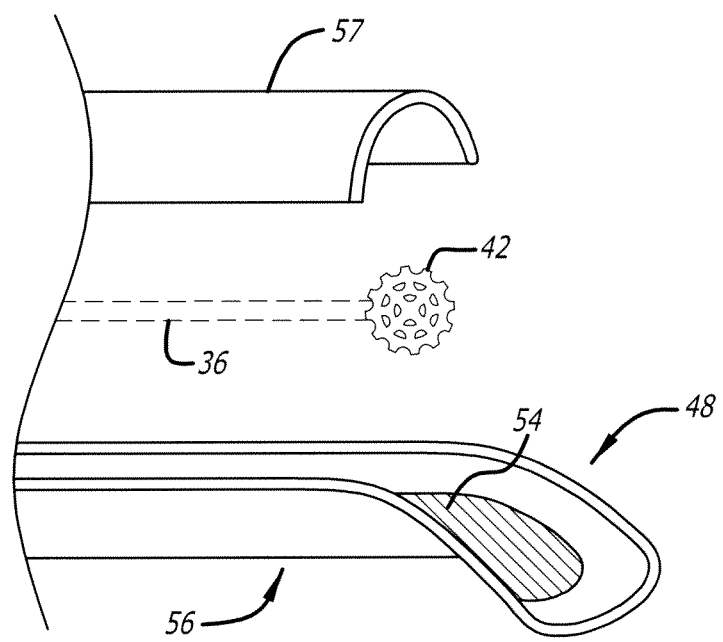
FIGS. 4A and 4B illustrate partial views of an exemplary implementation of a surgical tool and system.
Figure 4B:
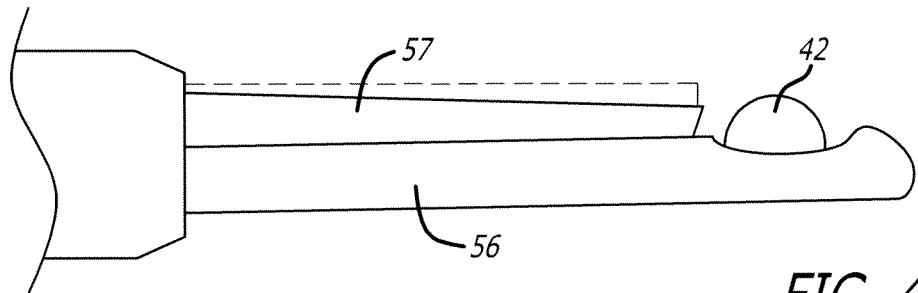

FIG. 3 illustrates a distal end of a retractor 48 is shaped so as to be tubular towards the proximal end 46 and a partial or semi cylindrical wall at the distal (remote) end 48. In some instances the shape will allow the retractor 44 to at least partially surround the length of the resector 34, but also to provide for retraction of the tissue at the distal end 48. FIGS. 4A and 4B illustrate a multi-part retractor 48 forming a cylindrical tube from two semi-cylindrical elements. On at least one inner surface a coating of material 54 that is thermally may be added a protection against any heat which may be generated from the resecting process. The ventral retractor element 56 protects neural elements as previously described. In this implementation it is the dorsal retractor element 57 that articulates to expose the resector tip 42.

Figure 5A:
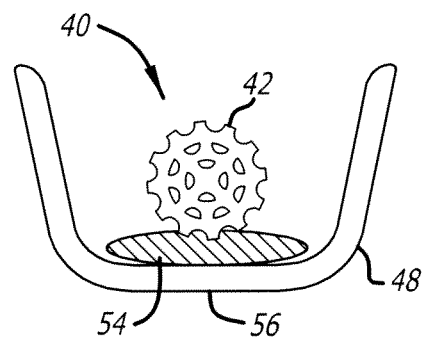
FIGS. 5A and 5B are partial views of an exemplary implementation of a resecting tool.
Figure 5B:
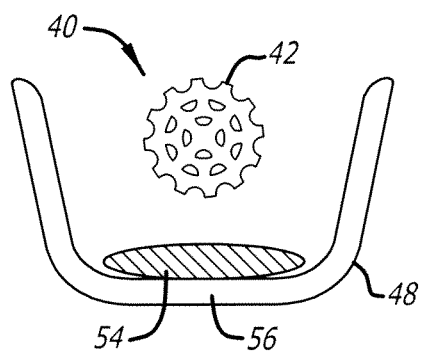

In its "off" or resting position, the distal end of the resector 40 may rest against the inner surface of the distal end of the retractor 48. This is illustrated in FIG. 5A. As shown in FIG. 5B when the resector is "on," meaning that the resector tip 42 is rotating, the distal end visa vie at least the ventral side of the retractor 48 is moved in a downward direction away from the distal tip of the resector 42. This provides the retraction of the tissue away from the resector tip 42 when it is activated and in motion. As noted previously to address possible damage to tissue at least the bottom portion of the inner surface of the distal end of the retractor 48 may be provided with a coating of material 54 that is thermally insulating and/or electrically insulating. Such materials include, but are not limited to, ceramics, polyethylene, pyrolytic carbons, biodegradable polylactic acid, polyglycolic acid, polycaprolactone, copolymers, and other plastics.

In addition to the retractor 44, the resecting tool can also include irrigation and suction capabilities as shown in FIG. 3, which will allow for the removal of detritus and provide for better visualization of the increased cross-sectional diameter of the spinal canal. The suction and irrigation can be provided through a separate channel 52 located within the retractor 44 or as an adjacent cylindrical opening on either side of the retractor (not shown). The hollow conduit 52 will allow for irrigation and also removal of bony or ligamentous detritus. To facilitate delivery of irrigation fluid and/or suction of detritus from the working site, multiple holes 55 may be located at the distal end of the housing of the retractor 48.

In addition to irrigation and suction, means for providing illumination at the distal end of the resecting tool can be provided. LEDs, fiber optic, or other well-known methods for providing illumination to the field can be included.

In addition to illumination, suction and irrigation capabilities, the device can include a camera. The camera can be provided through a separate attachment to the device or through a separate channel in the device itself.

The camera will allow real-time imaging of the resection to take place. This allows for the surgeon to directly visualize the procedure as it is being performed. The ability to visualize the resection is vital and provides the surgeon with accurate visualization of the decompression, neural foraminal decompression, and/or removal of disk and/or osteophyte or ligament resection being performed. Such real-time imaging will also provide more accurate decompressions to take place without having to resect too little or too much bone.

The camera will also facilitate the monitoring and taping of such procedures. This material can be then transmitted to or stored at local or more remote sites. Sites may include the central region for the spinal stenosis registry where data can be stored on all patients, including their initial questionnaire that relates to symptoms of neurogenic claudication preoperatively, the degree of intraoperative decompression that was completed, and the postoperative improvement seen at weeks, months, and years after the procedure. By recording this data, it is the hoped that the spinal stenosis registry will create a better understanding of neurogenic claudication and the amount of bone that is needed to be resected and how quickly the bone will re-accumulate. Such factors may include, but are not limited to, degree of osteoporosis, activity level, thickness of the lamina or neural foramen, etc.

Figure 6A:
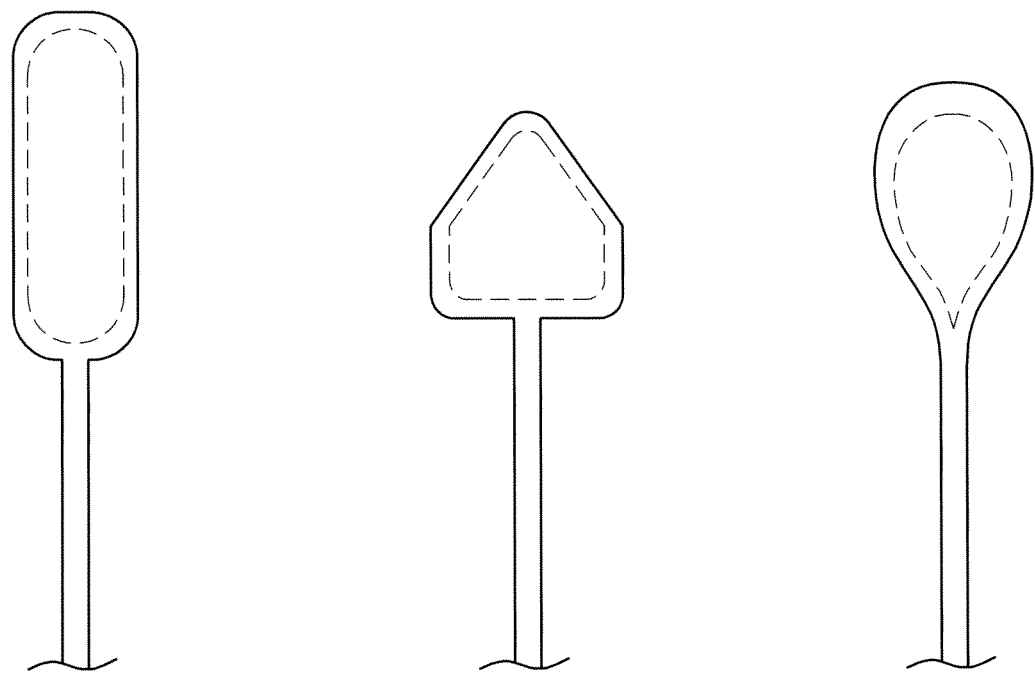
FIGS. 6A and 6B illustrate aspects of exemplary implementations of dissection tools and retractor shapes.
Figure 6B:

In addition to the retractor, there may be provided an optional additional dissecting tool that can be used as an extension to provide further separation of the dura from the ligament or the undersurface of the lamina or facets. By freeing up the dura and creating this space it allows the resecting tools to work with impunity in this very tight and delicate area. The additional instrument to free up the dura can be attached to the retractor or be supplied independently such that a dissecting tool is applied to the handpiece in place of the burr/retractor combination. The dissecting tool could be made to tilt or otherwise move in response to footpedal release of compressed air in the handpiece. A variety of shapes, sizes, and arc diameters may be provided, as illustrated in FIGS. 6A and 6B. The dissecting tools of FIG. 6A have a variety of shapes and are advantageously configured with slightly blunt and rounded edges. FIG. 6B illustrates a variety of cross sections, which may be used both for the end of the retractor or the end of a dissecting tool. The materials are advantageously biocompatible, which would include but are not limited to, metals such as nitinol, stainless steel, titanium, ceramic, tantalum and other non-biodegradable materials such as polyethylene, Teflon, pyrolytic carbons, polylactic acid, polyglycolic acid, polycaprolactone, copolymers, and other plastics.

The resecting tool can also include an angulating resector and/or angulating retractor to better access the area or surface to be resected. In one embodiment of the present invention, for example, the proximal end of the resector can angulate to angles including, but not limited to, 30°, 45°, or 60° relative to the handpiece. The proximal of the retractor may also angulate in unison with the proximal end of the resector to push the neural tissue away from the area or surface to be resected.

Figure 7A:
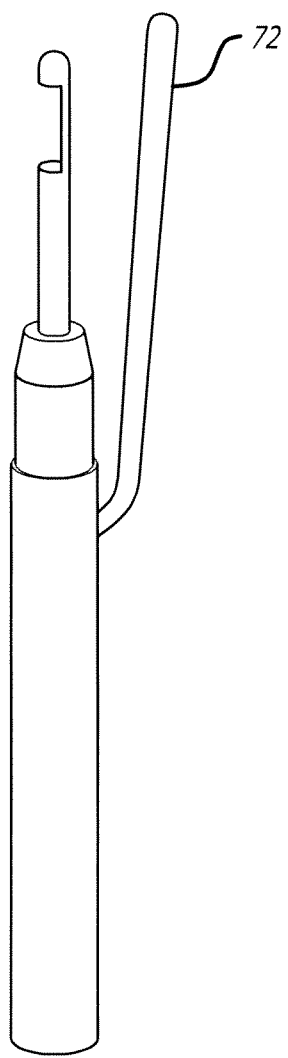
FIGS. 7A-7C are perspective views of an exemplary implementation of a surgical system and tool.
Figure 7C:
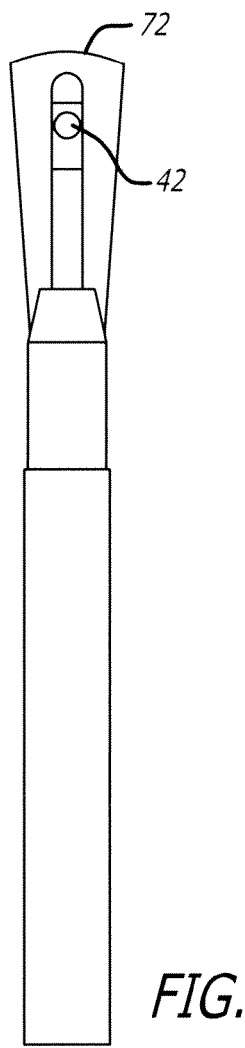
Figure 7B:
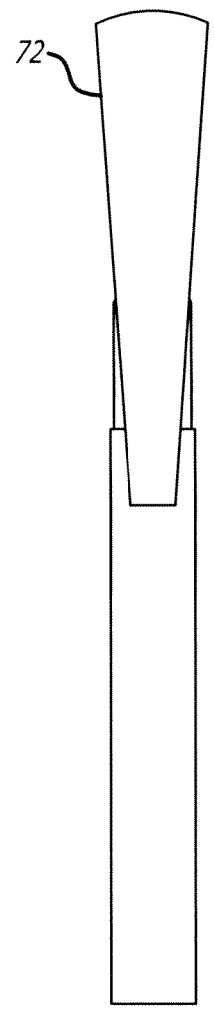
Figure 8A:
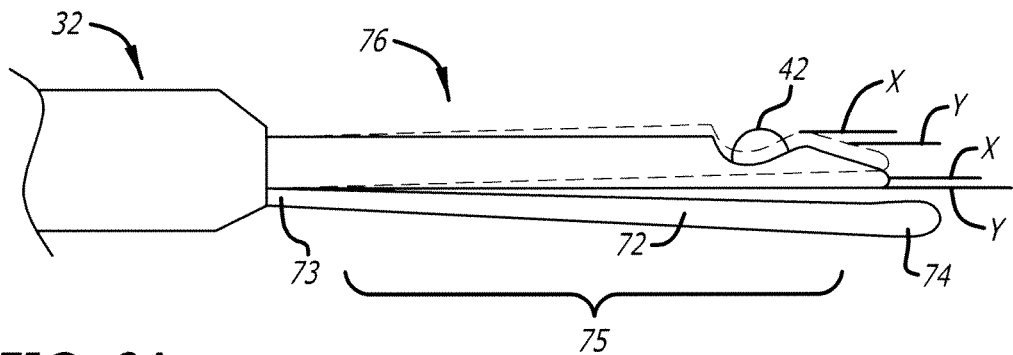
FIGS. 8A and 8C are a partial side and a side cut away and view of an exemplary implementation of a surgical tool and system.
Figure 8B:
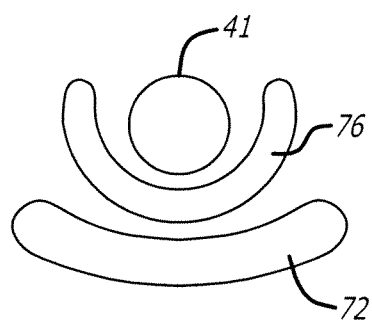
FIG. 8B is a front view of the surgical tool and system of FIG. 8A along line A-A.
Figure 8C:
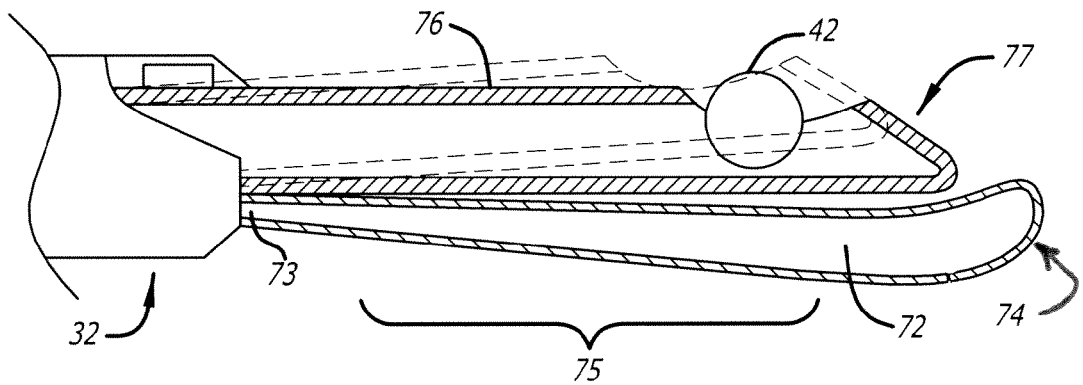
Figure 8D:
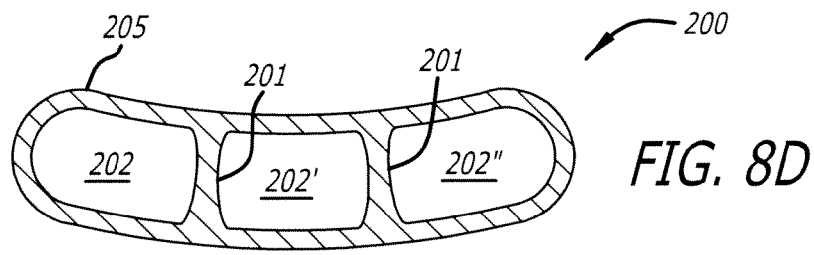
FIGS. 8D is a cut-away view of some aspects of a balloon retractor.

Referring now to FIGS. 7A through 7C, there is an exemplary implementation of a surgical resecting tool and system. The resecting tool has a retractor in the form of an inflation means. In some instances an expanding balloon retractor 72. The balloon retractor has a proximal end 73 and a distal end 74, and an inner and outer surface and for purposes of retraction a ventral side 75. The proximal end of the balloon retractor 73 may be releasably anchorable near the proximal end of the resector. At least part of the balloon retractor is moveable relative to the resector, at least via inflation. The resector tip at the distal end of the resector can remove bone, ligament, or other tissues without injuring the surrounding neural elements, which will be on the ventral side, below the retractor. By keeping the dorsal side of the surgical tool against the tissue needing to be resected and having the ventral side of the surgical tool (which terminates at the ventral side of the balloon 75) capable of retracting the surrounding tissue away from the site where resection is occurring, unattended tissue damage is minimized.

The shape of the balloon retractor may be varied to accommodate areas in the spinal canal, spinal laminar junction, or into the neural foramen.

When inflated, the balloon retractor on the ventral surface will provide a downward force to push the neural elements out of the way.

When the resector is "on", the cutting or resecting tip is moving (rotating for a burr and reciprocating for a rasp) coincident with the "on" of the resecting tool the balloon retractor 72 is inflated to expand in a downward direction away from the resector tip. Those of ordinary skill in the art will recognize that the disclosure also includes varying the balloon morphology to match desire use. Variations include balloon material, stiffness, lubricity, texture, shape, firmness, and dimensions to provide for retraction of the neural elements.

Illustrated in FIGS. 8A-8D are exemplary implementations of the resecting tool with balloon retraction 72 and resector shield 76. The resecting tool provides a body such as a handpiece 32 an inflatable means such as a balloon retractor 72 and a resector shield 76. The resector shield 76 is movably affixed to the a body whereby it may be moved between "X-X" position (the safety position wherein the resecting tip 42 is shielded) and "Y-Y" position (the engaged position wherein the resecting tip 42 is exposed to the tissue, bone or ligament that requires resection). The shield tip 77 is at the distal end of the resector shield 76 and may be used to facilitate movement of tissue, dissection, and displacement to allow access of the resector to the target area. Both the ventral and dorsal sides of the shield may be used to move, retract, displace, and dissect.

Disclosed herein are inflatable means 200, such as balloon retractors 72, bladders or air chambers for protecting, retracting and/or shielding at least neural element during use of a resecting tool (such as those detailed herein). An inflatable means 200 can also be introduced in combination with other retractors to provide additional retraction to the thecal sac or nerve root sleeves in the event a more posterolateral decompression is warranted. Inflatable retractors are configurable in a plurality of sizes and shapes with the ability to bend and also expand. The bending may be via zones or by control of air pressure. The expansion indicates a change on a cross-sectional diameter of the inflated space within the inflatable means. Such changes in diameter may include changes from about 0.1 to about 10 mm in at least a portion of a cross sectional diameter. The inflatable means such as a single chamber, balloon or bladder may be circular, elliptical, ovoid, flattened, in cross section. A multi-chambered inflatable retractor means of more than one balloon or bladder type has a wall structure 201 between chambers 202, 202' and 202" can provide stiffness and control of shape (See FIG. 8D). The wall structure may be sealed to prevent communication between chambers or it may be unsealed (to allow fluid communication of air between chambers). The chambers need not be adjacent (i.e. two noncontiguous chambers 202 and 202" may be in fluid communication). Chambers may be substantially the same thickness or of varied thickness, height, width, length, and surface morphology and texture.

Chambers 202, 202' and 202" may be selectively filled or released as a group or individually to adjust shape and stiffness. The inflatable means may be single layer or multilayered. The outer surface 25 of the inflatable means 200 may be single or multi-layered. The portion of the outer surface exposed to the body may be lubricious, textured sticky, slicked, provided to have a high or low coefficient of friction. The outer surface may be a composite of textures and frictional zones. The outer surface may also have tougher, harder, and/or denser portions (which may be edges, or levers) affixed to or formed as part of the outer surface which may be used to promote retraction and separation.

Figure 9A:
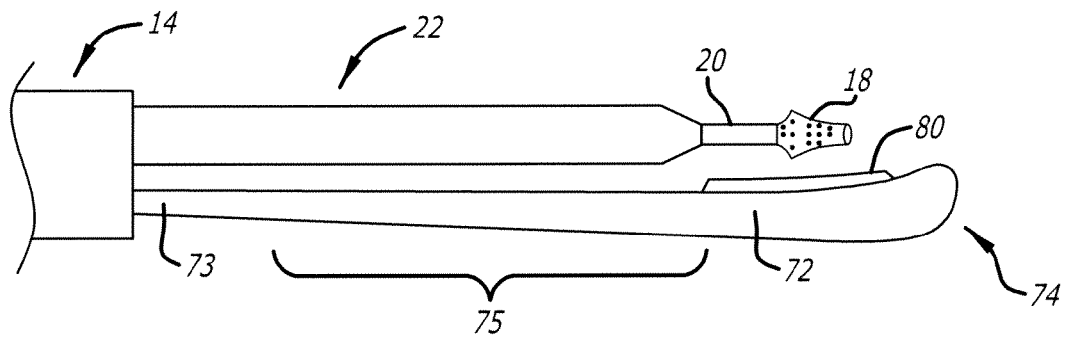
FIG. 9A is a partial side view of an exemplary implementation of a surgical tool.
Figure 9B:
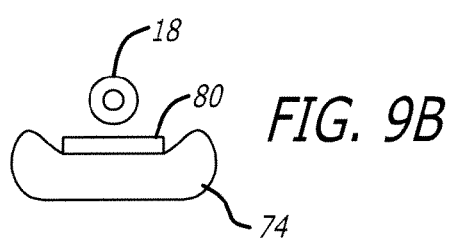
FIG. 9B is a front view of the surgical tool and system FIG. 9A along line A-A.
Figure 10:
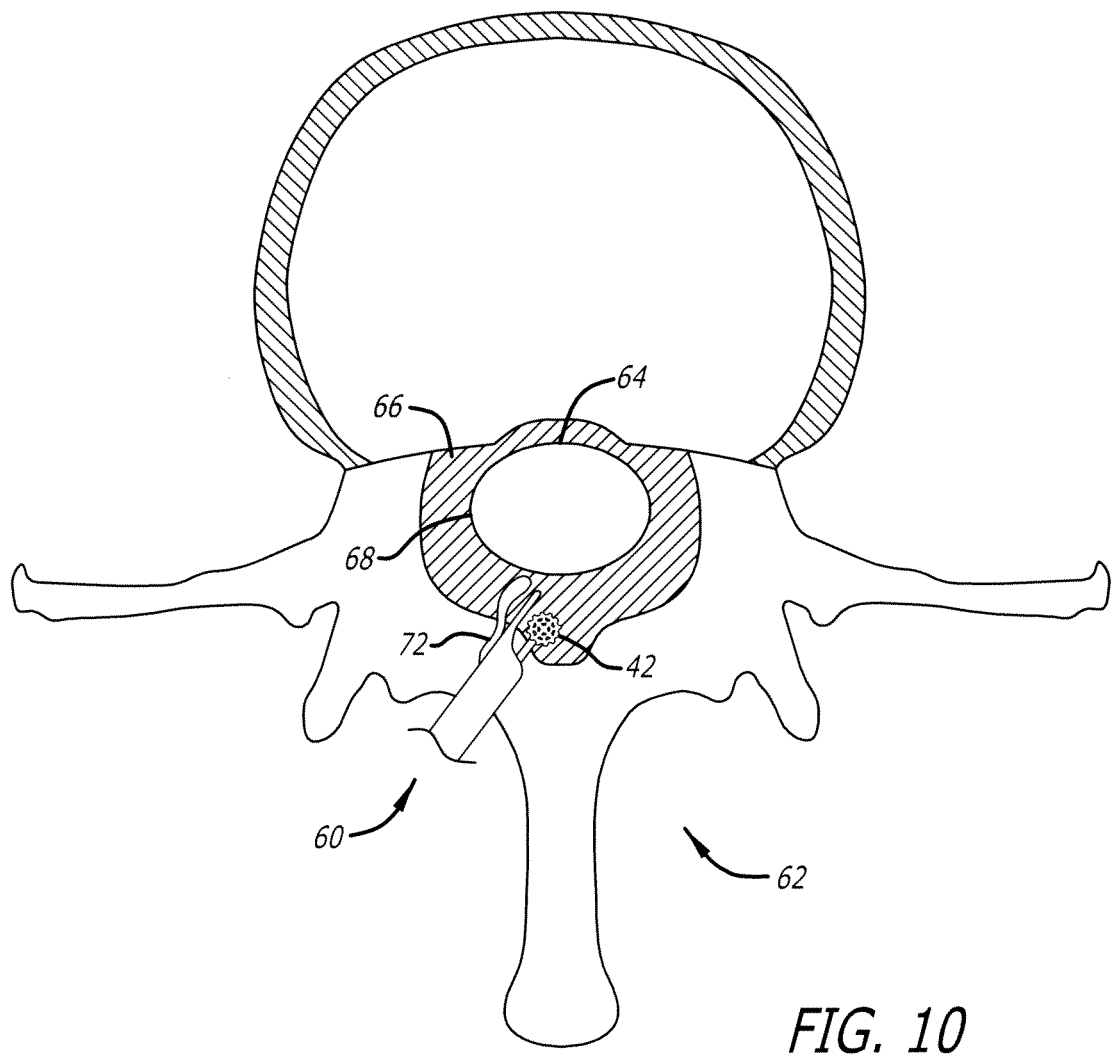
FIG. 10 illustrates an exemplary implementation a method of using a surgical system and tool.

Illustrated in FIGS. 9A-9B are exemplary implementations of a resecting tool with balloon retraction 72. A balloon retractor 72 on the surgical tool described in reference to FIG. 1 provides for retraction of neural elements and provides separation of the burr 18 from the neural elements. A tough coating 80 of a hard material is added to the dorsal side of the balloon retractor opposite the burr 18 to prevent accidental puncture of the balloon retractor 72 by the burr 18. The coating maybe plastic, metal, ceramic or laminate, including combinations of the same. Some aspects of exemplary implementations of the surgical tool and system of the disclosure are generally illustrated in FIG. 10. Generally, the surgeon first performs a minimal incision to the spine. Such an incision would provide access between the spinous processes down through the interspinous ligament and through the area between the lamina, 60, 62. The spinal cord or thecal sac 64 lies within the vertebral canal 66 and is covered by three membranes, the outermost layer being the dura 68.

The distal end of the resector tool is delivered to site. During insertion, the tool is in its "off" or resting position, and the distal end of the resector tool rests against the inner surface of the distal end of the balloon retractor as described herein. When the distal end of the resecting tool is in the desired position, the resector is turned "on" to rotate the burr. The inflated balloon expands and retracts neural elements away and protects them during resection of the tissue.

The burr is used to remove bone, ligament or other tissues and the resector and shield elements are provided to reduce injury to the surrounding neural elements, especially the dura 68, which is on the ventral side of the device, below the retractor. By keeping the resecting tip against the tissue targeted for resection and having the retractor retracting the surrounding tissue away from the site where resection is targeted, unintended tissue damage may be reduced/minimized.

During insertion, the resecting tool will normally be in its "off" or resting position, and the distal end of the resector tool rests against the inner surface of the distal end of the balloon retractor and near the area targeted for resection. When the distal end of the resecting tool is in the desired position, the resector is turned "on" to move the resecting tip. Before, or commensurate with, turning on the resecting tip, the inflatable retractor is inflated. By keeping the resecting tip near the tissue targeted for resection and having the retractor retracting the surrounding tissue away from the site where resection is targeted, unintended tissue damage may be reduced/minimized.

The burr is used to remove bone, ligament or other tissues while the retractor is used to move, cover and/or protect neural elements especially the dura, which is on the ventral side of the device, below the inflatable retractor.

The foregoing description details certain embodiments of the invention. It will be appreciated, however, that no matter how detailed the foregoing appears in text, the invention can be practiced in different ways. As is also stated above, it should be noted that the use of particular terminology when describing certain features or aspects of the invention should not be taken to imply that the terminology is being redefined herein to be restricted to including any specific characteristics of the features of aspects of the invention with which the terminology is associated. The scope of the invention should therefore be construed in accordance with the appended claims and any equivalents thereof.

What is claimed:

1. A cutting device comprising in combination:
    a handle;
    a cutting means with a cutting tip
    a shield at least partially surrounding a portion of the cutting means, the shield movable in a lateral direction relative to and away from at least a ventral side of the cutting means whereby the shield is moved from a first position where the cutting tip is not exposed to a second position where the cutting tip is exposed; and
    an inflatable retractor situated on one side of the cutting means with a top, bottom, outer surface and interior.

2. The device of claim 1 wherein the cutting means is at least one of a shaft driven rotating burr, shaft driven reciprocating rasp and a shaft driven moving file.

3. The device of claim 1 wherein the inflatable retractor comprises a single chamber.

4. The device of claim 3 further comprising a section of hard material on the inflatable retractor opposite the cutting means, wherein the hard material is resistant to cutting tip damage.

5. The device of claim 1 wherein the inflatable retractor comprises at least two connected chambers.

6. The device of claim 5 wherein the at least two connected chambers are inflated and deflated without fluid communication between each other.

7. The device of claim 5 wherein the at least two connected chambers have fluid communication between each other.

8. The device of claim 5 further comprising a section of hard material on the inflatable retractor opposite the cutting tip, wherein the hard material is resistant to cutting tip damage.

9. A cutting device comprising in combination:
    a hand piece;
    a cutting means with a cutting tip; and,
    an angulating retractor situated on one side of the cutting means with a top, bottom, outer surface and interior, wherein the retractor comprises a resecting shield that at least partially surrounds a portion of the cutting means, the resecting shield movable in a lateral direction relative to and away from at least a ventral side of the cutting means whereby the resecting shield is moved from a first position where the cutting, means is not exposed to a second position where the cutting means is exposed; and,
    wherein said angulating retractor is pivotally movable relative to said handpiece with the distal end of the retractor being movable laterally away from the distal end of the cutting means and the proximal end of the retractor rotates or tilts at the handpiece.

10. The device of claim 9 wherein the cutting means is at least one of a shaft driven rotating burr, shaft driven reciprocating rasp and a shaft driven moving file.

11. The device of claim 9 wherein at least one of air, motors, wheels, belts, levers and gears tilt said retractor thereby exposing said cutting means and wherein at least one of air, motors, wheels, belts, levers and gears cause said cutting means to move.

12. The device of claim 11 further comprising;
    at least one actuator which starts the tilt of said retractor; and,
    at least one actuator which starts the motion of said cutting means.

13. The device of claim 12, wherein a single actuator starts the tilt of said retractor and starts the motion of said cutting means.

* * * * *